(12) United States Patent
Eggers et al.

(10) Patent No.: US 9,983,284 B2
(45) Date of Patent: May 29, 2018

(54) MRI WITH DIXON-TYPE WATER/FAT SEPARATION AND PRIOR KNOWLEDGE ABOUT INHOMOGENEITY OF THE MAIN MAGNETIC FIELD

(71) Applicant: KONINKLIJKE PHILIPS N.V., Eindhoven (NL)

(72) Inventors: Holger Eggers, Hamburg (DE); Clemens Bos, Best (NL)

(73) Assignee: Koninklijke Philips N.V., Eindhoven (NL)

( * ) Notice: Subject to any disclaimer, the term of this patent is extended or adjusted under 35 U.S.C. 154(b) by 997 days.

(21) Appl. No.: 14/368,467

(22) PCT Filed: Dec. 10, 2012

(86) PCT No.: PCT/EP2012/074944
§ 371 (c)(1),
(2) Date: Jun. 24, 2014

(87) PCT Pub. No.: WO2013/098060
PCT Pub. Date: Jul. 4, 2013

(65) Prior Publication Data
US 2014/0350386 A1 Nov. 27, 2014

Related U.S. Application Data

(60) Provisional application No. 61/581,287, filed on Dec. 29, 2011.

(30) Foreign Application Priority Data

Dec. 29, 2011 (EP) ..................................... 11196022

(51) Int. Cl.
*G01V 3/00* (2006.01)
*G01R 33/48* (2006.01)
(Continued)

(52) U.S. Cl.
CPC .......... *G01R 33/4828* (2013.01); *A61B 5/055* (2013.01); *G01R 33/56563* (2013.01)

(58) Field of Classification Search
CPC ................................................. G01R 33/4828
(Continued)

(56) References Cited

U.S. PATENT DOCUMENTS 4,661,775 A 4/1987 Kormos
5,823,959 A 10/1998 Rasche
(Continued)

FOREIGN PATENT DOCUMENTS

JP 61275644 A 12/1986

OTHER PUBLICATIONS

Glover, G.H., "Multipoint Dixon Technique for Water and Fat Proton and Susceptibility Imaging" Journal of Magnetic Resonance Imaging, vol. 1, Jan. 1991, pp. 521-530.
(Continued)

*Primary Examiner* — Louis Arana

(57) ABSTRACT

A method and an apparatus for MR imaging of at least two chemical species having different MR spectra enables Dixon water/fat separation in cases in which a large field-of-view is required. The method includes the steps of: a) generating at least one echo signal by subjecting a body placed in the examination volume of a MR device to an imaging sequence of RF pulses and switched magnetic field gradients; b) acquiring the at least one echo signal; c) separating signal contributions of the at least two chemical species to the at least one acquired echo signal on the basis of a spectral model and prior knowledge about the spatial variation of the main magnetic field Bo in the examination volume; and d) reconstructing a MR image from the signal contributions of at least one of the chemical species.

3 Claims, 2 Drawing Sheets

(51) Int. Cl.
*G01R 33/565* (2006.01)
*A61B 5/055* (2006.01)

(58) Field of Classification Search
USPC .................................................. 324/307, 309
See application file for complete search history.

(56) References Cited

U.S. PATENT DOCUMENTS

| | | | |
|---|---|---|---|
| 6,263,228 | B1 | 7/2001 | Zhang |
| 6,445,184 | B1 | 9/2002 | Tanttu |
| 6,750,650 | B2 | 6/2004 | Kiefer |
| 2009/0131781 | A1 | 5/2009 | Dahnke et al. |
| 2010/0002926 | A1 | 1/2010 | Dahnke et al. |
| 2015/0212183 | A1* | 7/2015 | Beck .................. G01R 33/4818 324/309 |
| 2016/0061918 | A1* | 3/2016 | Yeo .................... G01R 33/5607 324/309 |
| 2016/0313422 | A1* | 10/2016 | Boernert ............ G01R 33/5602 |

OTHER PUBLICATIONS

Kanayama, S. et al "Ultrafast Single-Shot Water and Fat Separated Imaging with Magnetic Field Inhomogeneites", IEEE Transations on Information and System, Information and Systems Socity. vol. E77-D, No. 8, Aug. 1994, pp. 918-924.

Yeung, H.N. et al "Separation of True Fat and Water Images by Correcting Magnetic Field Inhomogeneity in Situ", Radiology, Radiological Society of North America, vol. 159, No. 3, Jun. 1986, pp. 783-786.

Ma, Jingfei "Dixon Techniques for Water and Fat Imaging" Journal of Magnetic Resonance Imaging, vol. 28, No. 3, Sep. 2008, pp. 543-558.

Yu, Huanzhou et al "Single Acquisition Water-Fat Separation: Feasibility Study for Dynamic Imaging", Magnetic Resonance in Medicine, vol. 55, No. 2, Feg. 2006, pp. 413-422.

Berglund, Johan et al "Two-Point Dixon Method with Flexible Echo Times", Magnetic Resonance in Medicine, vol. 65, No. 4, Jan. 2011, pp. 994-1004.

Rybicki, Frank J. et al "Fast Three-Point Dixon MR Imaging of the Retrobulbar Space with Low-Resolution Images for Phase Correction: Comparison with Fast Spin-Echo Inversion Recovery Imaging", AJNR Am J. Neuroradiol, vol. 22, Oct. 2001, pp. 1798-1800.

Jacob, Mathews et al "Algebraic Decomposition of Fat and Water in MRI", IEEE Transactions on Medical Imaging, vol. 28, No. 2, Feb. 2009, pp. 173-184.

Reeder, S.B. et al "Multicoil Dixon Chemical Species Separation with an Iterative Least-Squares Estimation Method", Magnetic Resonance in Medicine, vol. 51, No. 1, Jan. 2004, pp. 35-45.

Yu, Huanzhou et al "Multiecho Water-Fat Separation and Simultaneous R2* Estimation with Multifrequency Fat Spectrum Modeling", Magnetic Resonance in Medicine, vol. 60, Oct. 2008, pp. 1122-1134.

Reeder, S.B. et al "Iterative Decomposition of Water and Fat with Echo Asymmetry and Least-Squares Estimation (IDEAL): Application with Fast Spin-Echo Imaging", Magnetic Resonance in Medicine, vol. 54, No. 3, Sep. 2005, pp. 636-644.

Coombs, B.D. et al "Two-Point Dixon Technique for Water-Fat Signal Decomposition with B0 Inhomogeneity Correction", Magnetic Resonance in Medicine, vol. 38, No. 6, Dec. 1997, pp. 884-889.

Hammer, B.E. "Magnetic Field Mapping with An Array of Nuclear Magnetic Resonance Proves" Review of Scientific Instruments, vol. 67, No. 6, Jun. 1996, pp. 2378-2380.

Glover, G.H. et al "Three-Point Dixon Technique for True Water/Fat Decomposition with B0 Inhomogeneity Correction", Magnetic Resonance in Medicine, vol. 18, 1991, pp. 371-383.

* cited by examiner

MRI WITH DIXON-TYPE WATER/FAT SEPARATION AND PRIOR KNOWLEDGE ABOUT INHOMOGENEITY OF THE MAIN MAGNETIC FIELD

CROSS-REFERENCE TO PRIOR APPLICATIONS

This application is the U.S. National Phase application under 35 U.S.C. § 371 of International Application No. PCT/EP2012/074944, filed on Dec. 10, 2012, which claims the benefit of U.S. Provisional Patent Application No. 61/581,287, filed on Dec. 29, 2011 and European Patent Application No. 11196022.5, filed on Dec. 29, 2011. These applications are hereby incorporated by reference herein.

FIELD OF THE INVENTION

The invention relates to the field of magnetic resonance (MR) imaging. It concerns a method of MR imaging of a portion of a body placed in the examination volume of a MR device. The invention also relates to a MR device and to a computer program to be run on a MR device.

BACKGROUND OF THE INVENTION

Image-forming MR methods which utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

According to the MR method in general, the body of the patient to be examined is arranged in a strong, uniform magnetic field $B_0$ whose direction at the same time defines an axis (normally the z-axis) of the co-ordinate system on which the measurement is based. The magnetic field $B_0$ produces different energy levels for the individual nuclear spins in dependence on the magnetic field strength which can be excited (spin resonance) by application of an electromagnetic alternating field (RF field) of defined frequency (so-called Larmor frequency, or MR frequency). From a macroscopic point of view the distribution of the individual nuclear spins produces an overall magnetization which can be deflected out of the state of equilibrium by application of an electromagnetic pulse of appropriate frequency (RF pulse) while the magnetic field $B_0$ extends perpendicular to the z-axis, so that the magnetization performs a precessional motion about the z-axis. The precessional motion describes a surface of a cone whose angle of aperture is referred to as flip angle. The magnitude of the flip angle is dependent on the strength and the duration of the applied electromagnetic pulse. In the case of a so-called 90° pulse, the spins are deflected from the z axis to the transverse plane (flip angle 90°).

After termination of the RF pulse, the magnetization relaxes back to the original state of equilibrium, in which the magnetization in the z direction is built up again with a first time constant $T_1$ (spin lattice or longitudinal relaxation time), and the magnetization in the direction perpendicular to the z direction relaxes with a second time constant $T_2$ (spin-spin or transverse relaxation time). The variation of the magnetization can be detected by means of receiving RF coils which are arranged and oriented within an examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal (spin echo) in the receiving coils.

The paper "Multipoint Dixon Technique for water and fat protopn susceptbility imaign in JMRI 1(1991)521-530 concerns a multi-point Dixon technique. In this Dixon technique a spectral model tis employed hat retains the fat complex as a single line but allows the linewidth to differ from that of water.

SUMMARY OF THE INVENTION

In order to realize spatial resolution in the body, constant magnetic field gradients extending along the three main axes are superposed on the uniform magnetic field $B_0$, leading to a linear spatial dependency of the spin resonance frequency. The signal picked up in the receiving coils then contains components of different frequencies which can be associated with different locations in the body. The signal data obtained via the receiving coils correspond to the spatial frequency domain and are called k-space data. The k-space data usually include multiple lines acquired with different phase encoding. Each line is digitized by collecting a number of samples. A set of k-space data is converted to an MR image by means of Fourier transformation.

In MR imaging, it is often desired to obtain information about the relative contribution of different chemical species, such as water and fat, to the overall signal, either to suppress the contribution of some of them or to separately or jointly analyze the contribution of all of them. These contributions can be calculated if information from two or more corresponding echoes, acquired at different echo times, is combined. This may be considered as chemical shift encoding, in which an additional dimension, the chemical shift dimension, is defined and encoded by acquiring a couple of images at slightly different echo times. In particular for water-fat separation, these types of experiments are often referred to as Dixon-type of measurements. By means of Dixon imaging or Dixon water/fat imaging, a water-fat separation can be achieved by calculating contributions of water and fat from two or more corresponding echoes, acquired at different echo times. In general such a separation is possible because there is a known precessional frequency difference of hydrogen in fat and water. In its simplest form, water and fat images are generated by either addition or subtraction of the 'in phase' and 'out of phase' datasets. However, this so-called 2-point Dixon technique fails, when $B_0$ field inhomogeneities become larger. This is the case for many clinical applications at high $B_0$ fields where global shimming cannot completely compensate for local field variations. 3-point or 4-point Dixon techniques were developed to correct for these field inhomogeneities. These techniques provide, in addition to a water image and a fat image, a map of $B_0$ field inhomogeneities, the so-called $B_0$ map.

The retrospective separation of the contributions from the different chemical species to the acquired, composite MR signals in Dixon-type MR imaging commonly relies on a smooth spatial variation of the main magnetic field $B_0$. This general assumption is typically violated near large susceptibility gradients within the examination volume and also at locations remote from the iso-center of the main magnet coil of the used MR device. Corresponding imperfections of the main magnetic field $B_0$ may cause the retrospective separation of the signal contributions from the different chemical species to "swap", with the consequence that signal contributions from fat wrongly appear in the water image and vice versa. This limitation presently restricts the usable field of view further than in applications not requiring a separation of different chemical species.

From the foregoing it is readily appreciated that there is a need for an improved MR imaging technique. It is consequently an object of the invention to provide a method that enables Dixon water/fat separation in cases in which the field-of-view covers regions with large main magnetic field imperfections.

In accordance with the invention, a method of MR imaging of at least two chemical species having different MR spectra is disclosed. The method of the invention comprises the steps of:
 a) generating at least one echo signal by subjecting a body placed in the examination volume of a MR device to an imaging sequence of RF pulses and switched magnetic field gradients;
 b) acquiring the at least one echo signal;
 c) separating signal contributions of the at least two chemical species to the at least one acquired echo signal on the basis of a spectral model and prior knowledge about the spatial variation of the main magnetic field $B_0$ in the examination volume; and
 d) reconstructing a MR image from the signal contributions of at least one of the chemical species.

The invention addresses the above described limitations on the usable field-of-view in conventional Dixon-type MR techniques. The invention suggests including prior knowledge about the spatial variation of the main magnetic field $B_0$ in the signal separation step.

Such prior knowledge about the spatial variation of the main magnetic field $B_0$ may be gained from the design of the main magnet coil of the used MR device. For example, a simulation of $B_0$ can be performed on the basis of a model of the main magnet coil.

The prior knowledge may also be gained from measurements of the main magnetic field $B_0$, as they are typically performed at system installation during and after the static shimming of the main magnetic field $B_0$ by the placement of shim irons. In addition, knowledge about the magnetic field produced by the shim coils may be considered. These shim coils serve for dynamic shimming, i.e. a reduction of magnetic field inhomogeneities in a defined volume. The magnetic field $B_0$ they generate can also be simulated on the basis of a model of the shim coils and the currents they are driven with in a particular scan.

Moreover, the prior knowledge can be gained from measurements of the main magnetic field $B_0$ by means of magnetic field probes, either before or during a particular scan. Finally, such prior knowledge can also be gained from imaging, such as $B_0$ mapping scans performed for dynamic shimming.

The separation of the signal contributions according to the invention may involve a prediction of the phase evolution of the signal contributions of the at least two chemical species over the respective echo time according to the spatial variation of the main magnetic field $B_0$ and a corresponding demodulation of the acquired MR signal (in k-space or in image space). Preferably, the demodulation according to the predicted phase evolution is performed after a distortion correction of the acquired MR signals which compensates for misregistration arising from both imperfections of the main magnet and the gradient system of the used MR device. It is also possible to consider the predicted phase evolution as a local offset of the MR frequency. This enables subsequent application of further steps that rely on smoothness in, for example, region growing, iterative filtering, or the like procedures commonly employed for water and fat signal separation in Dixon-type applications.

After all, the method of the invention permits reliable separation of signal contributions from different chemical species far from the main magnet's iso-center in applications that require a large field-of-view, without increasing the susceptibility of the method to noise.

During the signal separation step according to the invention, a spectral model for the different chemical species is employed. Such models may approximate the fat spectrum by a single, dominant peak. However, this simple model may fail to provide an efficient fat suppression. This is because hydrogen atoms in fat are known to comprise multiple spectral peaks. It is also possible in accordance with the invention that the spectrum of one of the chemical species is modeled, for example, by a multi-peak spectral model, while another chemical species (for example water protons) may simply be modeled by a single-peak spectrum.

It has to be noted that the term "chemical species" has to be broadly interpreted in the context of the invention as any kind of chemical substance or any kind of nuclei having MR properties. In a simple example, the MR signals of two chemical species are acquired, wherein the chemical species are protons in the "chemical compositions" water and fat. In a more sophisticated example, a multi-peak spectral model actually describes nuclei in a set of different chemical compositions which occur in known relative amounts.

The method of the invention described thus far can be carried out by means of a MR device including at least one main magnet coil for generating a uniform, steady magnetic field $B_0$ within an examination volume, a number of gradient coils for generating switched magnetic field gradients in different spatial directions within the examination volume, at least one body RF coil for generating RF pulses within the examination volume and/or for receiving MR signals from a body of a patient positioned in the examination volume, a control unit for controlling the temporal succession of RF pulses and switched magnetic field gradients, and a reconstruction unit for reconstructing MR images from the received MR signals. The method of the invention can be implemented by a corresponding programming of the reconstruction unit and/or the control unit of the MR device.

The method of the invention can be advantageously carried out on most MR devices in clinical use at present. To this end it is merely necessary to utilize a computer program by which the MR device is controlled such that it performs the above-explained method steps of the invention. The computer program may be present either on a data carrier or be present in a data network so as to be downloaded for installation in the control unit of the MR device.

As explained above, the technique of the invention is primarily applicable to fat-suppressed MR imaging, water/fat MR imaging, and fat quantification with MR imaging. It is especially interesting for applications requiring the coverage of areas far away from the main magnet's iso-center, as in large field-of-view or off-center imaging. In the respective regions remote from the iso-center, the large variations of the main magnetic field $B_0$ may cause correspondingly large phase shifts of the individual signal contributions of the at least two chemical species to each of the acquired echo signals on the order of $\pi$, $2\pi$, or even more, depending on the echo time. Such large phase shifts would not be resolvable without prior knowledge on the spatial variation of the main magnetic field $B_0$ according to the invention.

The technique of the invention may advantageously be applied for MR imaging of the total spine, the upper extremities, the brachial plexus, and the abdomen. Today, commonly applied fat suppression techniques for these applications are short T inversion recovery (STIR) or spectral pre-saturation with inversion recovery (SPIR). STIR has a lower scan time efficiency and a sensitivity to relaxation rate ambiguities, and it is in general incompatible with contrast agents. Currently, techniques like SPIR, which suffer from a high sensitivity to main magnetic field inhomogeneities, have to be employed with contrast agents.

The technique of the invention may further be applied for first-pass contrast-enhanced MR angiography. Conventional fat suppression techniques are too time-consuming in this case and are typically replaced by a subtraction of pre- and post-contrast images, which increases the sensitivity to patient motion and prolongs the overall scan time.

The technique of the invention may further be applied for whole-body MR imaging for human body modelling, which gains relevance in diverse fields, such as attenuation correction for positron emission tomography and surface absorption rate prediction for multi-transmission MR imaging.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF EMBODIMENTS

Figure 1:
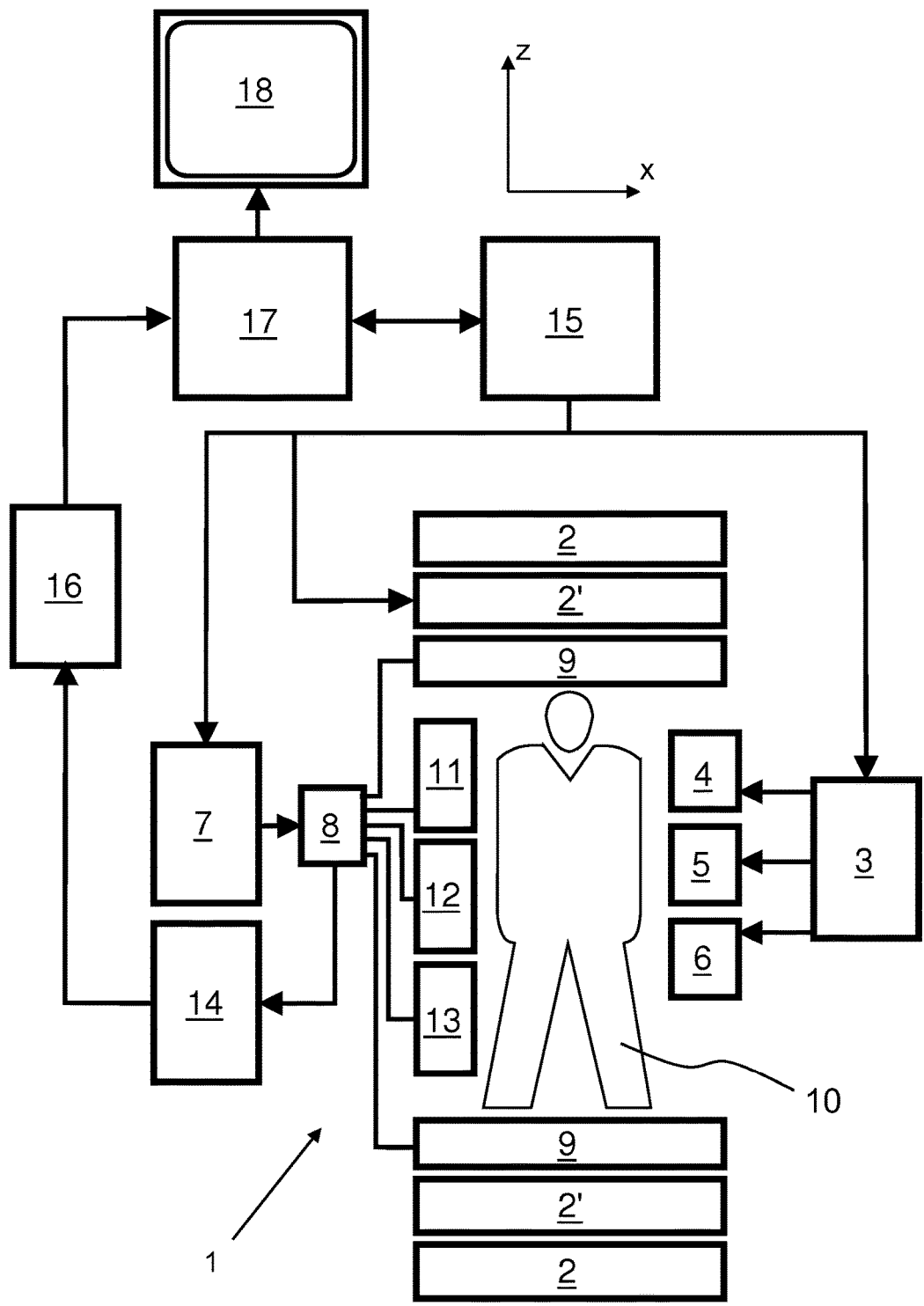
FIG. 1 shows a MR device for carrying out the method of the invention.

With reference to FIG. 1, a MR device 1 is shown. The device comprises superconducting or resistive main magnet coils 2 such that a substantially uniform, temporally constant main magnetic field $B_0$ is created along a z-axis through an examination volume. The device further comprises a set of ($1^{st}$, $2^{nd}$, and —where applicable— $3^{rd}$ order) shimming coils 2', wherein the current flow through the individual shimming coils of the set 2' is controllable for the purpose of minimizing $B_0$ deviations within the examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

More specifically, a gradient pulse amplifier 3 applies current pulses to selected ones of whole-body gradient coils 4, 5 and 6 along x, y and z-axes of the examination volume. A digital RF frequency transmitter 7 transmits RF pulses or pulse packets, via a send-/receive switch 8, to a body RF coil 9 to transmit RF pulses into the examination volume. A typical MR imaging sequence is composed of a packet of RF pulse segments of short duration which, together with any applied magnetic field gradients, achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals are also picked up by the body RF coil 9.

For generation of MR images of limited regions of the body 10 by means of parallel imaging, a set of local array RF coils 11, 12, 13 are placed contiguous to the region selected for imaging. The array coils 11, 12, 13 can be used to receive MR signals induced by body-coil RF transmissions.

The resultant MR signals are picked up by the body RF coil 9 and/or by the array RF coils 11, 12, 13 and demodulated by a receiver 14 preferably including a preamplifier (not shown). The receiver 14 is connected to the RF coils 9, 11, 12 and 13 via send-/receive switch 8.

A host computer 15 controls the shimming coils 2' as well as the gradient pulse amplifier 3 and the transmitter 7 to generate any of a plurality of MR imaging sequences, such as echo planar imaging (EPI), echo volume imaging, gradient and spin echo imaging, fast spin echo imaging, and the like. For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data are reconstructed into an image representation by a reconstruction processor 17 which applies a Fourier transform or other appropriate reconstruction algorithms, such as SENSE or SMASH. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

In an embodiment of the invention, first and second echo signals are generated by means of a dual gradient echo imaging sequence, wherein the echo time of the first echo is 1.8 ms while the echo time of the second echo is 3.1 ms. In a main magnetic field of 1.5 Tesla, the contributions of water and fat spins to the first echo signal are more out of phase, while they are more in phase at the time of the second echo signal. A plurality of first and second echo signals are generated and acquired with appropriate phase encoding in a common fashion in order to be able to reconstruct a complete MR image of the desired field-of-view.

Figure 2:
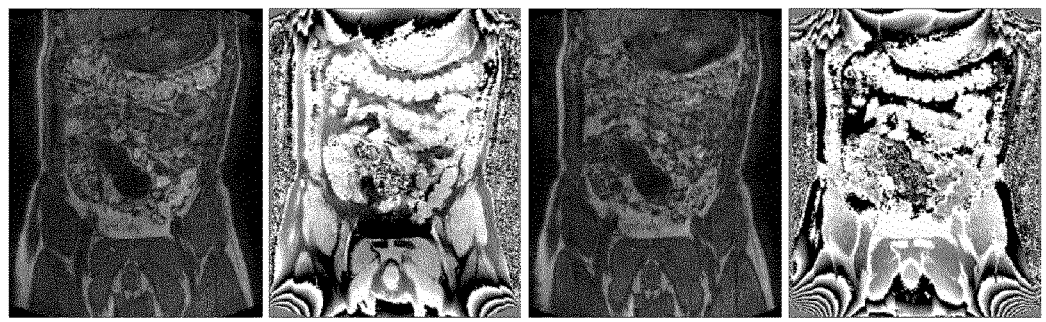
FIG. 2 shows magnitude and phase MR images reconstructed from echo signals acquired at two different echo times.

FIG. 2 shows magnitude and phase MR images for a selected slice from a three-dimensional volume, wherein the left MR images are reconstructed from the first echo signals, while the right MR images are reconstructed from the second echo signals. As can be seen in the phase MR images in FIG. 2, a rapid phase evolution from the first to the second echo time occurs in the corners of the field-of-view, i.e. in the regions of the legs in the abdominal images. This rapid phase evolution is due to strong spatial variations of the main magnetic field $B_0$ in the regions far remote from the iso-center of the main magnet 2.

The acquired complex echo signals S in image space are modeled by $$s = (W + cF)e^{i\varphi},$$

wherein W and F denote the water and fat signal contributions in image space, and $\varphi$ denotes a phase error. The complex factor c is given by $$c = \sum_m w_m e^{i\theta_m},$$

wherein in w denotes weights that add up to one and $\theta$ equals $2\pi \Delta f TE$, with $\Delta f$ being the offset in resonance frequency of the m peaks of the fat spectrum with respect to water and TE being the respective echo time.

Given prior knowledge about the spatial variation of the main magnetic field, denoted by $\Delta B_0$, the predicted phase evolution over the echo spacing $\Delta TE$ is:

$$e^{i\varphi'} = e^{i\gamma \Delta B_0 \Delta TE}$$

Hence, the prior knowledge about the magnetic field distribution can be used for demodulation of the composite complex echo signal $S_n$ at echo time $TE_n$ according to:

$$S'_n = S_n \left( e^{-i\varphi'} \right)^{n-1}$$

In this way, known strong spatial variations of the main magnetic field $B_0$ remote from the iso-center of the main magnet are eliminated, rendering the assumption of smoothness of the main magnetic field variation as a prerequisite for known high-quality water/fat separation algorithms valid again. While the first echo time is chosen as reference for the demodulation in this example, any other reference may be employed instead, most notably at MR signal excitation.

Figure 3:
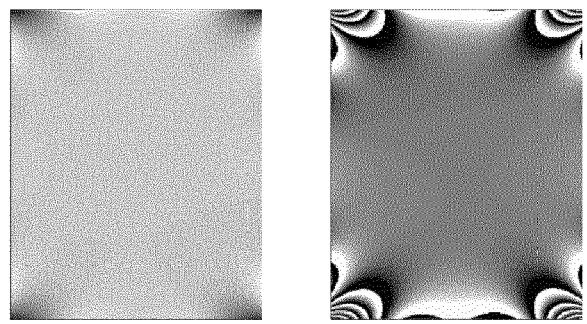
FIG. 3 illustrates a prior-knowledge $B_0$ map (left) and the predicted phase evolution (right) over the echo spacing applied in the acquisition of the MR images of FIG. 2.

The prior knowledge about the spatial variation of the main magnetic field $B_0$ can be gained from appropriate measurements of $B_0$ during installation of the main magnet. A corresponding map of $B_0$ is shown in FIG. 3 (left). The right image in FIG. 3 shows the phase evolution over the spacing of the echo signals predicted from the $B_0$ map.

Figure 4:
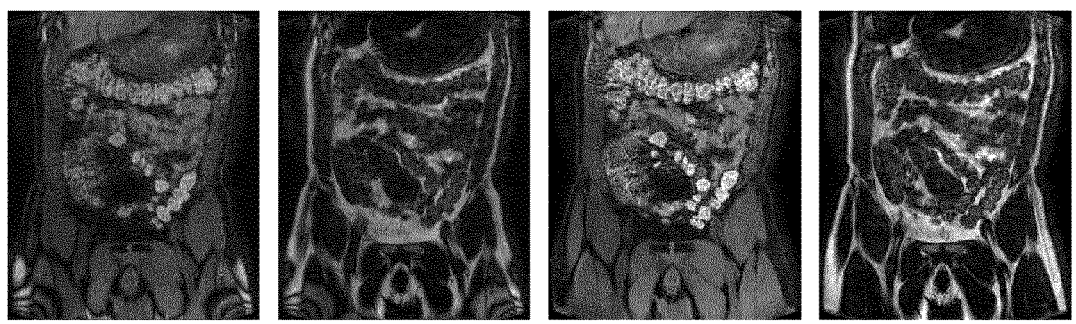
FIG. 4 shows water and fat images separated from the MR images of FIG. 2 without (left) and with (right) use of the prior-knowledge $B_0$ map of FIG. 3.

FIG. 4 shows water and fat images separated from the MR images of FIG. 2 without (left two images) and with (right two images) demodulation according to the spatial variation of the main magnetic field $B_0$ as shown in FIG. 3. Without phase demodulation strong image artifacts caused by the imperfections of the main magnetic field remote from the magnet's iso-center are visible in the regions of the legs. These artifacts are visible in both the water and the fat images. As is evident from FIG. 4, a substantial improvement of the image quality is obtained by the method of the invention. The artifacts visible in the left water and fat images are no longer visible in the right water and fat images reconstructed in accordance with the invention.

The invention claimed is:

1. A method of MR imaging of at least two chemical species having different MR spectra, the method comprising the steps of:

a) generating at least one echo signal by subjecting a body placed in the examination volume of a MR device to an imaging sequence of RF pulses and switched magnetic field gradients;

b) acquiring the at least one echo signal;

c) separating signal contributions of the at least two chemical species to the at least one acquired echo signal on the basis of a multi-peak spectral model for at least one of the chemical species and the prior knowledge about spatial variations of the main magnetic field $B_0$ in the examination volume; and wherein a phase evolution of the signal contributions of the at least two chemical species over the respective echo time on the order of $\pi$, $2\pi$, or more is predicted according to the spatial variations of the main magnetic field $B_0$, wherein the prediction of the phase evolution of the signal contributions of the at least two chemical species over the respective echo time is used to demodulate the phase of these signal contributions before the separation on the basis of the multi-peak spectral model, wherein the multi-peak spectral model on which the separation is based considers phase errors reflecting further main magnetic field variations, wherein the prior knowledge about the spatial variations of the main magnetic field $B_0$ is gained from:
   design parameters of a main magnet coil of the MR device and/or from shimming parameters;
   a measurement by means of magnetic field probes; or
   a $B_0$ map obtained from a separate MR scan; and d) reconstructing a MR image from the signal contributions of at least one of the chemical species.

2. An MR device including at least one main magnet coil configured to generate a steady magnetic field $B_0$ within an examination volume, a plurality of gradient coils configured to generate switched magnetic field gradients in different spatial directions within the examination volume, at least one RF coil configured to generate RF pulses within the examination volume and/or for receiving MR signals from a body of a patient positioned in the examination volume, a controller configured to control a temporal succession of RF pulses and switched magnetic field gradients, and a reconstruction processor configured to reconstruct MR images from the received MR signals, wherein the controller is configured to control the MR device to perform the following steps:

a) generating at least one echo signal by subjecting a body placed in the examination volume of the MR device to an imaging sequence of RF pulses and switched magnetic field gradients;

b) acquiring the at least one echo signal;

c) separating signal contributions of at least two chemical species having different MR spectra to the at least one echo signal on the basis of a multi-peak spectral model and the prior knowledge about spatial variations of the steady magnetic field $B_0$ in the examination volume; and wherein a phase evolution of the signal contributions of the at least two chemical species over a respective echo time on the order of $\pi$, $2\pi$, or more is predicted according to the spatial variations of the main magnetic field $B_0$, wherein the prediction of the phase evolution of the signal contributions of the at least two chemical species over the respective echo time is used to demodulate the phase of these signal contributions before the separation on the basis of the multi-peak spectral model;

wherein the prior knowledge about the spatial variations of the main magnetic field $B_0$ is gained from:
   design parameters of the magnetic coil of the MR device and/or from shimming parameters;
   a measurement by magnetic field probes; or
   a $B_0$ map obtained from a separate MR scan; and
wherein the multi-peak spectral model on which the separation is based considers phase errors reflecting further main magnetic field variations; and
d) reconstructing an MR image from the signal contributions of at least one of the chemical species.

3. A non-transitory computer-readable medium carrying a computer program configured to run on a control processor of an MR device to control the MR device to:
   generate an imaging sequence of RF pulses and switched magnetic field gradients;
   separate signal contributions of at least two chemical species having different MR spectra to the at least one echo signal on the basis of a multi-peak spectral model for at least one of the chemical species and prior knowledge about spatial variation of a main magnetic field $B_0$ in an examination volume of the MR device;

wherein a phase evolution of the signal contributions of the at least two chemical species over the respective echo time on the order of $\pi$, $2\pi$, or more is predicted according to the spatial variations of the main magnetic field $B_0$, wherein the prediction of the phase evolution of the signal contributions of the at least two chemical species over the respective echo time is used to demodulate the phase of these signal contributions before the separation on the basis of the multi-peak spectral model;
wherein the multi-peak spectral model on which the separation is based considers phase errors reflecting further main magnetic field variations;
wherein the prior knowledge about the spatial variations of the main magnetic field $B_0$ is gained from
   design parameters of a main magnet coil of the MR device and/or from shimming parameters;
   a measurement by magnetic field probes; or
   a $B_0$ map obtained from a separate MR scan; and
d) reconstructing a MR image from the signal contributions of at least one of the chemical species.

\* \* \* \* \*